United States Patent
Colarow et al.

(10) Patent No.: US 8,795,651 B2
(45) Date of Patent: Aug. 5, 2014

(54) METHOD OF FORTIFYING A FOODSTUFF WITH SIALIC ACID PRODUCING BACTERIA

(75) Inventors: Ladislas N. A. Colarow, Piestany (SK); Ivana Jankovic, Epalinges (CH); Norbert Sprenger, Savigny (CH); Jeroen Antonius Johannes Schmitt, Moudon (CH); Takoua Debeche, Corseaux (CH)

(73) Assignee: Nestec S.A., Vevey (CH)

( * ) Notice: Subject to any disclaimer, the term of this patent is extended or adjusted under 35 U.S.C. 154(b) by 47 days.

(21) Appl. No.: 13/128,550

(22) PCT Filed: Nov. 9, 2009

(86) PCT No.: PCT/EP2009/064842
§ 371 (c)(1),
(2), (4) Date: Jul. 7, 2011

(87) PCT Pub. No.: WO2010/052324
PCT Pub. Date: May 14, 2010

(65) Prior Publication Data
US 2011/0274672 A1   Nov. 10, 2011

(30) Foreign Application Priority Data
Nov. 10, 2008   (EP) ................................... 08168763

(51) Int. Cl.
*A61K 35/74* (2006.01)
(52) U.S. Cl.
USPC ............... 424/93.45; 435/252.9; 426/61
(58) Field of Classification Search
CPC .................................................. A23L 1/3014
See application file for complete search history.

(56) References Cited

U.S. PATENT DOCUMENTS

| | | | |
|---|---|---|---|
| 4,762,822 A * | 8/1988 | Ettinger | ............... 514/25 |
| 2004/0202765 A1 | 10/2004 | McMahon et al. | |
| 2005/0142643 A1 * | 6/2005 | Shiba et al. | ............... 435/85 |
| 2008/0003329 A1 | 1/2008 | Rueda et al. | |
| 2008/0003330 A1 | 1/2008 | Rueda et al. | |

FOREIGN PATENT DOCUMENTS

| | | | | |
|---|---|---|---|---|
| WO | WO03049547 | | 6/2003 | |
| WO | WO2006080822 | * | 8/2006 | ............... C12N 1/20 |

OTHER PUBLICATIONS

Almagro-Moreno et al., Insights into the evolution of sialic acid catabolism among bacteria, 2009, BMC Evolutionary Biology 9:118.*
Sakellaris et al., Presence of sialic acids in *Lactobacillus plantarum*, 1988, Biochemical and Biophysical Research Communications 155(3): 1126-1132.*
Parvez et al., Probiotics and their fermented food products are beneficial for health, 2006, Journal of Applied Microbiology 100(6): 1171-1185.*
Andreadaki, Studies of Biosynthetic and Catabolic Polyenzymic System of Sialylglycoconjugates in Prokaryotic and Eukaryotic Cells, 1995, National Technical University of Athens (Thesis), Abstract.*
Wang et al., "The file and potential of sialic acid in human nutrition," European Journal of Clinical Nutrition, vol. 57, No. 11, Nov. 2003, 99 1351-1369.

* cited by examiner

*Primary Examiner* — Jon P Weber
*Assistant Examiner* — Robert Yamasaki
(74) *Attorney, Agent, or Firm* — K&L Gates LLP

(57) ABSTRACT

The present invention generally relates to the field of sialic acids, in particular to the field of sialic acid enriched food products and their uses. One embodiment of the present invention relates to a food product enriched with food-grade sialic acid producing bacteria and/or a fraction thereof containing sialic acid.

7 Claims, 1 Drawing Sheet

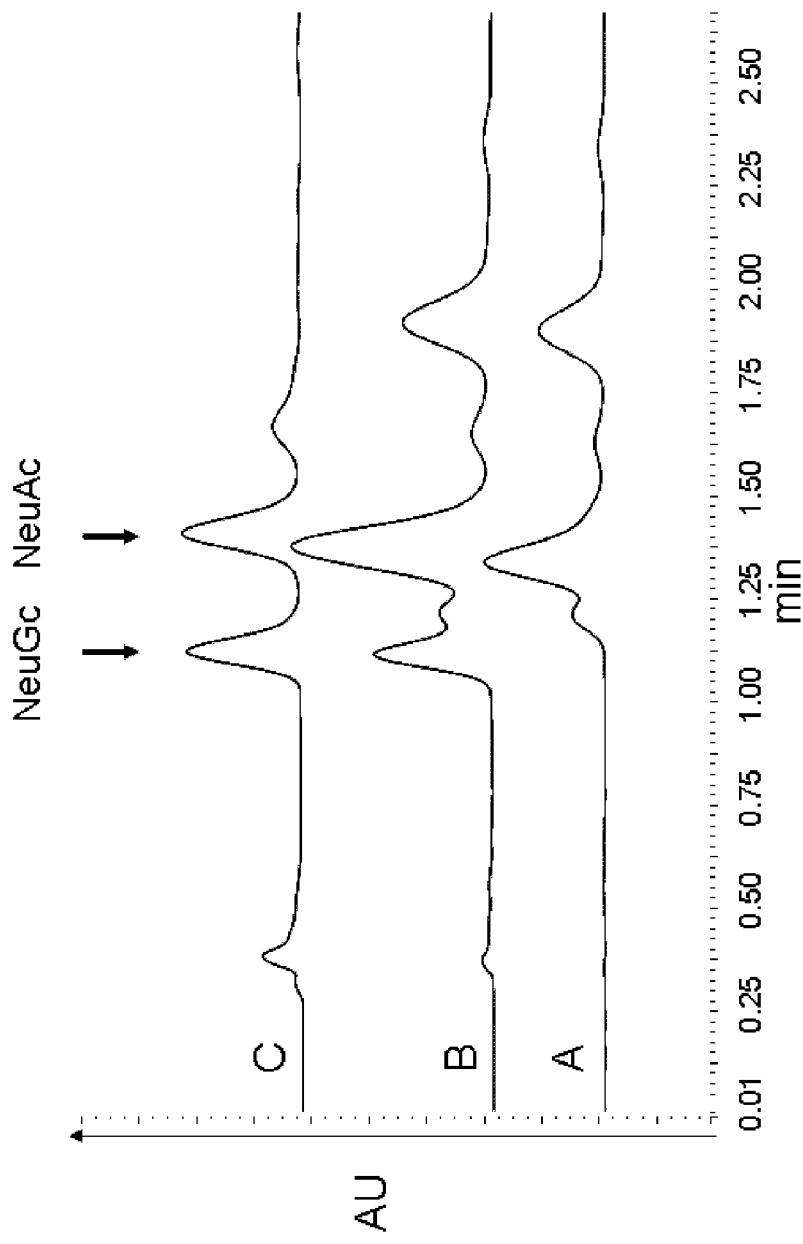
HPLC-fluorescence traces of NCC2936 (A); NCC2936 spiked with NeuAC and NeuGc standard (B); and NeuAC and NeuGc standard (C).

METHOD OF FORTIFYING A FOODSTUFF WITH SIALIC ACID PRODUCING BACTERIA

The present invention generally relates to the field of sialic acids, in particular to the field of sialic acid enriched food products and their uses. One embodiment of the present invention relates to a food product enriched with food-grade sialic acid producing bacteria and/or a fraction thereof.

Sialic acids (SiAc) are a family of charged nine carbon monosacharides derived from neuraminic acid (NeuAc). NeuAc is the only sialic acid normally formed in humans. In other vertebrates, for example N-glycolylneuraminic acids (NeuGc), are also present.

SiAc are indispensable for major cellular functions in vertebrates. As functional and structural component of gangliosides, they are synthesized in all tissues in mammals. However, fast growing cells and tissues subject to high apoptic and renewal rates might need additional NeuAc, provided for example by the diet.

Hence, today, sialic acids are frequently used, in particular in the field of infant nutrition. For example, a possible involvement of SiAc in the cognitive development of infants was summarized by Wang (Wang, B. and Brand-Miller, J. (2003) Eur. J. Clin. Nutr. November; 57(11):1351-69). Briefly, studies comparing breast-fed and formula-fed infants demonstrate that a higher NeuAc content of breast milk compared to a normal infant formula correlates with an increased NeuAc content of infants saliva and brain. However, behavioural effects of NeuAc supplementation in humans are not available. Nevertheless it is speculated that supplementation of cows milk with NeuAc would provide the cows milk with human milk attributes, which might have an impact on brain development of children.

Natural sources rich in SiAc, for example NeuAc, are, e.g., human milk, elephant milk, Indian buffalo milk, meat, eggs and fish. However, these sources are either not sufficient, not appropriate and/or too expensive, e.g. for the supplementation of dairy products with SiAc in the food industry today.

Thus, there is a great need for an alternative source of SiAc. The present inventors have addressed this need.

Consequently, it was the object of the present invention to provide the art with a source of SiAc that is easy to use in industrial environments, relatively inexpensive and allows it to isolate SiAc in a pure form or as a fraction that can be used in a food product.

The inventors were surprised that they could achieve this object by a use in accordance with claims 1 and 10 and by a sialic acid fortified foodstuff in accordance with claim 9.

The inventors found that SiAc can be easily provided from bacterial sources in a form suitable for food products.

SiAc are surface components of certain pathogens, which act as virulence factors. They are thought to function as an anti-recognition molecule by allowing the sialylated microorganism to masquerade, thereby evading host immune mechanisms. However, sialic acid obtained from pathogenic organisms is clearly not appropriate for food products, in particular for food products for infant nutrition.

Surprisingly, the present inventors have now identified food grade micro-organisms which synthesize SiAc, for example NeuAc, in particular when grown in standard medium.

The present invention hence relates to sialic acid obtained from food grade bacteria.

Consequently, one embodiment of the present invention is the use of naturally occurring sialic acid producing food grade bacteria or of at least one fraction thereof to fortify a foodstuff with sialic acid.

The invention also relates to the use of sialic acid obtained from food grade bacteria and/or of a bacterial fraction of food grade bacteria containing sialic acid to fortify a foodstuff with sialic acid.

The foodstuff may be enriched with sialic acid producing food grade bacteria, inactivated or alive, and/or with a fraction of the bacteria and/or their growth culture.

"Food grade" bacteria are bacteria that are approved for human or animal consumption.

A "fraction" of sialic acid producing food grade bacteria includes any part of the bacteria and/or of the bacterial culture comprising sialic acids. The term a "fraction" of sialic acid producing food grade bacteria also includes the media, the food grade bacteria were grown in, or parts thereof, since this medium will automatically contain bacterial SiAc. Further, the term "fraction" of sialic acid producing food grade bacteria also includes any SiAc containing fraction that is obtained when purifying SiAc from the bacterial culture.

In a preferred embodiment of the present invention the naturally occurring sialic acid producing food grade bacteria are viable in the foodstuff. This has the advantage that the bacteria can continue to produce sialic acid in the body, even after consumption of the foodstuff. Further, if the bacteria remain viable in the body, they will multiply and consequently the amount of sialic acid provided by the bacteria to the body will increase significantly.

For sterile products, it may also be preferred if the bacteria are present in an inactivated form, or if the product is enriched with pure bacterial SiAc or with a fraction of a culture of SiAc producing bacteria that does not contain any living bacteria.

In particular if the food grade bacteria are viable in the product, the bacteria or the at least one fraction thereof will be effective in any amount. If the bacteria reach the intestine alive, a single bacterium can be sufficient to achieve a powerful effect by colonization and multiplication.

However, for the foodstuff of the present invention it is generally preferred if the bacteria or the at least one fraction thereof are used in an amount sufficient to obtain in the food product a sialic acid content increase of 0.05-2 dry weight-%, preferably 0.4-1.5 dry weight-%, more preferably 0.6-1 dry weight-%.

The foodstuff of the present invention may be a nutritional composition, a nutraceutical, a drink, a food additive or a medicament. A food additive or a medicament may be in the form of tablets, capsules, pastilles or a liquid for example.

The foodstuff is preferably selected from the group consisting of milk based foodstuffs, in particular milk, whey, yoghurt, cheese, fermented products; infant formulas; solid baby food; follow-on formulas; toddler's beverages; fruit juices at least partially soluble drink mixes in powder form such as malt drinks, chocolate dinks, cappuccino, coffee drinks; chocolate; cereal products; sweets; cookies; gelatines.

Milk may be any milk obtainable from animal or plant sources and is preferably cows milk, human milk, sheep milk, goat milk, horse milk, camel milk or soy milk.

Instead of milk, also milk derived protein fractions or colostrum may be used.

The foodstuff may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. They may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. Further, they may contain an organic or inorganic carrier material suitable for oral or enteral administration as well as vitamins, minerals trace elements and other micronutrients in accordance with the recommendations of Government bodies such as the USRDA.

The foodstuff of the present invention may contain a protein source, a carbohydrate source and/or a lipid source.

Any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred.

If the foodstuff includes a fat source, the fat source more preferably provides 5% to 40% of the energy of the formula; for example 20% to 30% of the energy. DHA may be added. A suitable fat profile may be obtained using a blend of canola oil, corn oil and high-oleic acid sunflower oil.

A source of carbohydrates may more preferably provide between 40% to 80% of the energy of the composition. Any suitable carbohydrate may be used, for example sucrose, lactose, glucose, fructose, corn syrup solids, maltodextrins, and mixtures thereof.

The food grade bacteria are preferably selected from the group consisting of lactobacilli.

The inventors found that lactobacilli produce in particular large amounts of SiAc if the lactobacilli are producing N-acetylneuraminate lyase and/or N-acetylneuraminate aldolase.

Particularly preferred lactobacilli species that can be used for the purpose of the present invention are *Lactobacillus sakei, Lactobacillus plantarum* and/or *Lactobacillus salivarius*. Particular good results were are obtainable with bacteria selected from the group consisting of *Lactobacillus sakei* NCC 121, *Lactobacillus sakei* NCC 2935, *Lactobacillus sakei* NCC 2934, *Lactobacillus sakei* NCC 166, *Lactobacillus sakei* NCC 170, *Lactobacillus sakei* NCC 1393, *Lactobacillus sakei* NCC 1428, *Lactobacillus sakei* NCC 1511, *Lactobacillus sakei* NCC 2937, *Lactobacillus plantarum* NCC 2936, *Lactobacillus plantarum* NCC 252 or mixtures thereof.

Any bacterial fraction can be used for the purpose of the present invention. Particular preferred fractions are fractions obtainable by growing the cells in a growth medium, harvesting the cells, hydrolysing the cells under acidic conditions and collecting the supernatant which contains the sialic acid.

For example, one of the following methods can be used:

Method 1: After 16 h of growth at 37° C. in API medium (peptone 1%, yeast extract 0.5%, polysorbate 80 0.1%, ammonium citrate 0.2%, sodium acetate 0.5%, magnesium sulphate 0.01%, manganese sulphate 0.005% and dipotassium phosphate 0.2%, glucose 1%), the cells were harvested, and washed once in water. Sialic acids were released from the cells by hydrolysis in 2M acetic acid at 80° C. for 3 h. The supernatant obtained after centrifugation was lyophilized.

Method 2: The cells were grown in API medium (see above) for 16 h at 37° C. In 1l of fermentation medium, 250 g trichloric acid was added and stirred for 1 h at room temperature. After centrifugation of the cells, 1l of aceton was added to the supernatant and incubated overnight at 4° C. and centrifuged again. The precipitate was washed with 50% aceton and resuspended in water. The pH was adjusted to 7 centrifuged again. The extract was dialysis against water and lyophilized.

Method 3: After 16 h growth at 37° C. in API medium (see above), bacterial cells were washed twice with cold phophate buffered saline (137 mM NaCl, 2.7 mM KCl, 8.1 mM $Na_2HPO4$, 1.5 mM $KH_2PO_4$, pH7.4) and once with 0.1M pyridine acetate (pH5). Bacteria were resuspended in 0.1V of prewarmed pyrimidine acetate (0.1M, pH5) and incubated at 37° C. for 1 h. The supernatant obtained after centrifugation was lyophilized.

Any sialic acid may be used for the purposes of the present invention. However, it is preferred if the sialic acid has the following formula

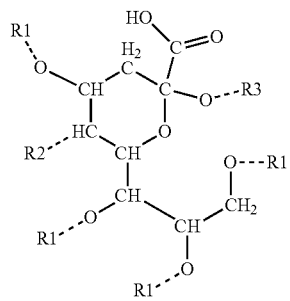

R1 = H, acetyl, lactyl, methyl, sulfate, phospate, anhydro, sialic acid, fucose, glucose, or galactose
R2 = N-acetyl, N-glycolyl, amino, hydroxyl, N-glycolyl-O-acetyl, or N-glycolyl-O-methyl
R3 = H, galactose, N-acetylglucosamine, N-acetylgalactosamine, sialic acid, or N-glycolylneuraminic acid R1 may be selected from the group consisting of H, acetyl, lactyl, methyl, sulfate, phosphate, anhydrosialic acid, fucose, glucose and/or galactose.

R2 may be selected from the group consisting of N-acetyl, N-glycolyl, amino, hydroxyl, N-glycolyll-O-acetyl, and/or N-glycolyl-O-methyl.

R3 may be selected from the group consisting of H, galactose, N-acetylglucosime, N-acetylgalactosamine, sialic acid, and/or n-glycolylneuraminic acid.

The groups in position R1 may be identical or different from each other. Similarly, the groups in position R2 may be identical or different from each other as may the groups in position R3.

In a particularly preferred embodiment of the present invention, the sialic acid is N-acetylneuraminic acid with R1=H, R2=N-acetyl and R3=H.

The present invention also relates to a sialic acid fortified foodstuff comprising naturally occurring sialic acid producing food grade bacteria or a fraction thereof. The sialic acid fortified foodstuff may have the same features as described above for the use of the present invention.

A foodstuff is fortified with sialic acid, if sialic acid or bacteria producing sialic acid are added to the foodstuff. For example, by fortification the amount of sialic acid that might be naturally present in the foodstuff is increased by at least 10 weight-%, preferably at least 50 weight-% even more preferred at least 100 weight-%.

The foodstuff of the present invention may be used to provide nutrition to a subject, for example to counterbalance a lack of endogenous sialic acid production. In particular in growing organisms the requirements for sialic acids often exceed the body's own endogenous sialic acid production. Hence sialic acid supplemented food products will help to support a subjects development. A lack of endogenous sialic acid production may, however, also occur in subjects, which are not growing anymore.

The present invention consequently also relates to the foodstuff of the present invention for use in the provision of nutrition to a subject. The foodstuff may be for use in counterbalancing a lack of endogenous sialic acid production.

Consequently the subject matter of the present invention is intended for humans or animals, in particular companion animals, pets and/or livestock. The subject matter of the present invention is in general not limited to any particular age group. The foodstuff may be administered to mothers during pregnancy and lactation, to treat the infant. It may also be administered to infants, children, teenagers, adults or elderly subjects. It is preferred however, to provide the foodstuff to infants.

The role and potential of sialic acid in human nutrition was summarized by Wang, B. and Brand-Miller, J. (2003) Eur. J. Clin. Nutr. November; 57(11):1351-69.

The present inventors have recently found that the administration of the foodstuff of the present invention to a subject leads to an elevated sialylation in the brain, in particular in aged subjects. This is seen for example by an increased sialylation of ganglioside (sialyl-lactosylceramides) enriched brain preparations. Sialylation and especially gangliosides are important factors in stabilizing the neuronal integrity and in allowing for neuronal plasticity in the central and peripheral nervous system.

It was also found that the administration of the foodstuff of the present invention, preferably to the elderly, leads to an elevated sialylation in the gastro intestinal tract (GIT), in particular in the proximal and distal colon mucosa. Here the modification of mucin sialylation affects the physico-chemical properties of the mucosal barrier. Additionally, glycolipid-bound sialylation was found to be augmented as seen by increased levels of gangliosides in the colon.

It was furthermore observed that the administration of the foodstuff of the present invention to a subject leads to an improved cell-mediated immune response. Concomitantly, 11-2 levels upon in vitro stimulation of spleenocytes by lectin ConA were augmented in subjects who consumed the foodstuff of the present invention compared to control subjects. This effect was more pronounced in infants and children than in the elderly.

The foodstuff of the present invention and/or the sialic acid obtained from food grade bacteria may consequently be used for the treatment or prevention of neurodegeneration, in particular in adults. It may also be used to improve cognitive performance and/or to support brain development, in particular in children.

Further applications of the foodstuff of the present invention and/or the sialic acid obtained from food grade bacteria are to support the immune system, in particular to boost immunity, and/or to improve gut function.

Particular clinical pathologies that can be treated or prevented with the foodstuff of the present invention and/or the sialic acid obtained from food grade bacteria include for example inflammatory bowel disease, intestinal bowel syndrome, nervous system degenerative pathologies such as dementia or Alzheimer's disease, post-infective auto destructive immune diseases, and/or GIT neuron degradation.

Consequently, the foodstuff of the present invention and/or the sialic acid obtained from food grade bacteria can for example promote healthy growth and healthy ageing; support brain development in infants and children; improve cognitive functioning; prevent or counteract cognitive decline and/or neurodegeneration, for example due to aging, illness or stress; support immune maturation and homeostasis; increase sialylation, for example in aged people, e.g., by providing dietary NeuAc for immunprotection; for reducing low-grade inflammations, for improving the gut barrier; and/or for suppressing systemic inflammations.

The sialic acid supplemented foodstuff of the present invention can contribute to optimum supplies of SiAc to the newborn, for example in maternal milk or infant formulae; to an optimal CNS development; to restore a circumstantial SiAc deficit, e.g., during pregnancy, lactation, and/or in cases of malnutrition.

Those skilled in the art will understand that they can freely combine all features of the present invention described herein, without departing from the scope of the invention as disclosed. In particular, features described for the uses of the present invention may be applied to the foodstuff of the present invention and vice versa.

Further advantages and features of the present invention are apparent from the following Examples and Figures.

FIG. 1 shows 1,2-Diamino-4,5-methylendioxybenzene dihydrochloride (DMB) chromatograms: *L. plantarum* NCC2936 (A); NCC2936 spiked with NeuAC and NeuGc standard (B); and NeuAC and NeuGc standard (C).

EXAMPLES

Methods

Bacterial Strains and their Production

Bacterial strains were obtained from the Nestle Culture Collection (NCC) and were grown on API medium (peptone 1%, yeast extract 0.5%, polysorbate 80 0.1%, ammonium citrate 0.2%, sodium acetate 0.5%, magnesium sulphate 0.01%, manganese sulphate 0.005% and dipotassium phosphate 0.2%, glucose 1%). After 16 h of growth at 30° C., bacteria were harvested and freeze-dried.

Detection of SiAc

SiAc were detected using a modified method of Jourdian et al. (1971) *J Biol Chem* 246: 430-435. Briefly, 10 μl of 0.04M periodic acid was mixed with 50 μl of sample or 50 μl of NeuAc standard (0, 20, 40, 60, and 100 μg/ml) and incubated for 35 minutes in an ice bath. 125 μl of the fresh mix composed of 0.04 mg of $CuSO_4$ in 6 ml 28% HCl+1 ml 6% resorcinol+3 ml $H_2O$ was added and incubated for 5 minutes at 4° C. The samples were boiled for 15 minutes and cooled down. 125 μl of 95% tert-butanol was added and incubated for 3 minutes at 37° C. to stabilize the colour. The scoring was done visually, by comparing the intensity of the blue colour of the samples with the standards of different concentrations.

Quantification of SiAc 1,2-Diamino-4,5-methylendioxybenzene dihydrochloride (DMB) method: A bacterial sample was dissolved in water to obtain an expected total sialic acid concentration of about 2 μg/mL. A 200 μL aliquot of this solution was hydrolysed by adding 200 μL formic acid (1.0 M) and heating at 80° C. for 2 h to release all bound sialic acids. The sialic acids were then derivatised with 1,2-diamino-4,5-methylenedioxybenzene dihydrochloride (DMB), a fluorescent label which is specific for α-keto acids. The derivatisation was carried out by adding 200 μL of a solution of DMB (7.0 mM in 1.4 M acetic acid containing 0.75 M 2-mercaptoethanol and 18 mM sodium hydrosulphite) to a 200 μL aliquot of the hydrolysed sample, the mixture was then heated at 80° C. for 50 min. The derivatised samples (5 μL) were injected on to a reversed phase HPLC column (Zorbax SB-Aq, 3.5 μm, 4.6×50 mm) and eluted using a mobile phase of water/methanol/acetic acid (75/25/0.05$_{(v/v/v)}$) flowing at 2.0 mL/min. The column eluant was monitored using fluorsesence detection ($\lambda_{ex}$=373 nm, $\lambda_{em}$=448 nm). Quantification was performed by preparing a calibration curve from sialic acid of known concentration and comparing peak areas from the sample with those of the standards.

Identification of NeuAc (GC-MS Analysis)

Methyl glycosides were prepared from a weighed amount of sample by treating with 1 M HCl in methanol (25 drops) at 80° C. for 15 h followed by re-N-acetylation with pyridine (5 drops) and acetic anhydride (5 drops) in methanol (20 drops) at room temperature for 1 h. The samples were then per-O-trimethylsilylated by the treatment with Tri-Sil (10 drops, Pierce) at 80° C. (15 minutes). These procedures were carried out as previously described (Merkle, R. K. and I. Poppe (1994) Methods Enzymol. 230:1-15; York, W. A. at al (1986) Methods Enzymol 118:3-40). GC/MS analysis of the TMS methyl glycosides was performed on an HP 5890 GC interfaced to a 5970 MSD, using a DB-1 column (30 m×0.25 mm ID).

Results

Detection of SiAc Producing Bacteria

Bacteria from the Nestle Culture Collection were screened for SiAc production using a periodic method. The following strains were identified as particular efficient in SiAc production and were deposited under the Budapest treaty.

| | |
|---|---|
| *Lactobacillus sakei* NCC 121 | (deposit number CNCM I-4020) |
| *Lactobacillus sakei* NCC 2935 | (deposit number CNCM I-4064) |
| *Lactobacillus sakei* NCC 2934 | (deposit number CNCM I-4025) |
| *Lactobacillus sakei* NCC 166 | (deposit number CNCM I-4066) |
| *Lactobacillus sakei* NCC 170 | (deposit number CNCM I-4067) |
| *Lactobacillus sakei* NCC 1393 | (deposit number CNCM I-4022) |
| *Lactobacillus sakei* NCC 1428 | (deposit number CNCM I-4023) |
| *Lactobacillus sakei* NCC 1511 | (deposit number CNCM I-4024) |
| *Lactobacillus sakei* NCC 2937 | (deposit number CNCM I-4065) |
| *Lactobacillus plantarum* NCC 2936 | (deposit number CNCM I-4026) |
| *Lactobacillus plantarum* NCC 252 | (deposit number CNCM I-4021) |

Identification of SiAc Type

The dried powders of the SiAc producing strains were prepared as described in Material and Methods. The same powders were analysed using two different methods: DMB and GC-MS:

a) FIG. 1 represents typical chromatogram of analysed strains (NCC 2936) produced using DMB method. Using this method we identified a peak running at almost the same retention time as N-acetyl neuraminic acid (NeuAc), but showing a slight retention time shift. No visible peak close to N-glycolyl neuraminic acid (NeuGc) was detected. Such a shift may occur if the sample contains something which binds to the stationary phase of the column. Such a binding reduces interaction of the analyte with the stationary phase and thus the retention time shifts. Alternatively, the SiAc might be modified by an additional chemical group and, therefore, shows an altered retention time.

To test if the peaks were shifted due to interfering compounds in the sample, we performed a "spiking" experiment. A defined amount of NeuAc standard was added to one sample preparation and the sample run on the HPLC again. The retention time of the peak observed in the spiked sample was much closer to that of the standard NeuAc peak probably due to a dilution effect. Only one peak was detected in the NeuAc spiked sample, indicating that the standard added to the sample runs at the same position with the original sample peak. Thus, we conclude that this peak most probably represents NeuAc and that initially observed retention time shift was likely due to interfering compounds in the sample and not due to a modification of NeuAc.

b) An additional evidence that bacteria produce NeuAc was obtained in a GC-MS analysis. Using this method, the glycosyl composition of bacterial samples was analysed (Table 1). As a result, the SiAc present in the bacterial samples was confirmed to be NeuAc.

TABLE 1

Glycosyl composition analysis of bacterial samples

| Sample | Glycosyl residue | Mass (µg) | Mol %[1] |
|---|---|---|---|
| *L. sakei* NCC 2934 | Ribose (Rib) | 4.0 | 4.3 |
| | Galactose (Gal) | 23.2 | 20.7 |
| | Glucose (Glc) | 42.8 | 38.3 |
| | N-acetyl glucosamine (GlcNAc) | 40.2 | 36.0 |
| | N-acetyl neuraminic acid (NANA) | 1.5 | 0.7 |
| | Σ = | 111.7 | |
| *L. sakei* NCC 2935 | Ribose (Rib) | 1.8 | 6.4 |
| | Galactose (Gal) | 1.7 | 4.9 |
| | Glucose (Glc) | 16.9 | 49.8 |
| | N-acetyl glucosamine (Glc NAc) | 12.8 | 37.8 |
| | N-acetyl neuraminic acid (NANA) | 0.6 | 1.1 |
| | Σ = | 33.8 | |
| *L. sakei* NCC 2937 | Ribose (Rib) | 1.8 | 6.2 |
| | Rhamnose (Rha) | 4.7 | 14.6 |
| | Galactose (Gal) | 1.4 | 4.1 |
| | Glucose (Glc) | 9.7 | 27.3 |
| | N-acetyl glucosamine (GlcNAc) | 16.4 | 46.4 |
| | N-acetyl neuraminic acid (NANA) | 0.6 | 1.4 |
| | Σ = | 34.6 | |
| *L. plantarum* NCC 2936 | Ribose (Rib) | 3.9 | 5.3 |
| | Galactose (Gal) | 5.9 | 6.8 |
| | Glucose (Glc) | 56.4 | 64.8 |
| | N-acetyl glucosamine (GlcNAc) | 18.2 | 21.0 |
| | N-acetyl neuraminic acid (NANA) | 2.3 | 2.1 |
| | Σ = | 86.7 | |

[1]Values are expressed as mole percent of total carbohydrate.

Quantification of SiAc

Quantification of SiAc in bacterial samples was done with DMB method and periodic assay method. DMB is quantitative method, while periodic assay was used for semi-quantitative analysis of the samples. The precise quantification using periodic assay was not possible because of the high background colour that interfered with the spectrophotometric reading of the results. The results of the quantification performed on the same batch of bacteria are presented in Table 2.

TABLE 2

NeuAc content in bacterial samples

| Strain | DMB method | Periodic assay |
|---|---|---|
| *L. sakei* NCC 2934 | 0.16 | 0.27 |
| *L. sakei* NCC 2935 | 0.13 | 0.21 |
| *L. sakei* NCC 2937 | 0.14 | 0.21 |
| *L. plantarum* NCC 2936 | 0.16 | 0.21 |

The SiAc content is expressed as % of bacterial dry matter

The invention claimed is:

1. A method of fortifying a foodstuff with sialic acid, the method comprising adding a naturally occurring sialic acid producing food grade bacteria containing sialic acid to the foodstuff to fortify the foodstuff with sialic acid, wherein the food grade bacteria is *Lactobacillus sakei* and the sialic acid is N-acetylneuraminic acid.

2. The method of claim 1, wherein the bacteria are used in an amount sufficient to obtain in the food product a sialic acid content increase of 0.05-2 dry weight-%.

3. The method of claim 1, wherein the bacteria produce N-acetylneuraminate aldolase.

4. A method of fortifying a foodstuff with sialic acid, the method comprising adding a naturally occurring sialic acid producing food grade bacteria containing sialic acid to the foodstuff to fortify the foodstuff with sialic acid, wherein the naturally occurring sialic acid producing food grade bacteria are viable so that they produce sialic acid in a body after consumption of the foodstuff, the food grade bacteria is *Lactobacillus sakei* and the sialic acid is N-acetylneuraminic acid.

5. A method of fortifying a foodstuff with sialic acid, the method comprising adding a naturally occurring sialic acid producing food grade bacteria containing sialic acid to the foodstuff to fortify the foodstuff with sialic acid, wherein the bacteria is selected from the group consisting of *Lactobacillus sakei* NCC 121, *Lactobacillus sakei* NCC 2935, *Lactobacillus sakei* NCC 2934, *Lactobacillus sakei* NCC 166, *Lactobacillus sakei* NCC 170, *Lactobacillus sakei* NCC 1393, *Lactobacillus sakei* NCC 1428, *Lactobacillus sakei* NCC 1511, *Lactobacillus sakei* NCC 2937, *Lactobacillus plantarum* NCC 2936, *Lactobacillus plantarum* NCC 252 and mixtures thereof.

6. A method of fortifying a foodstuff with sialic acid, the method comprising adding a naturally occurring sialic acid producing food grade bacteria containing sialic acid to the foodstuff to fortify the foodstuff with sialic acid, wherein the sialic acid has the following formula

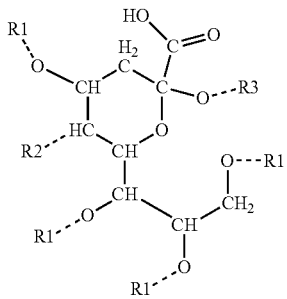

R1 = H, acetyl, lactyl, methyl, sulfate, phospate, anhydro, sialic acid, fucose, glucose, or galactose
R2 = N-acetyl, N-glycolyl, amino, hydroxyl, N-glycolyl-O-acetyl, or N-glycolyl-O-methyl
R3 = H, galactose, N-acetylglucosamine, N-acetylgalactosamine, sialic acid, or N-glycolylneuraminic acid.

7. The method of claim 6, wherein the sialic acid is N-acetylneuraminic acid (R1=H, R2=N-acetyl, R3=H).

* * * * *